US006875465B2

(12) United States Patent
Bishop et al.

(10) Patent No.: US 6,875,465 B2
(45) Date of Patent: Apr. 5, 2005

(54) METHOD OF DECORATING A SUBSTRATE BY APPLICATION OF GOLD NANOPARTICLES

(75) Inventors: Peter Trenton Bishop, Reading (GB); Patricia Ann Marsh, Kidlington (GB); Bénédiete Jeanne Suzanne Thiébaut, Henly on Thames (GB); Alison Mary Wagland, Wallington (GB)

(73) Assignee: Johnson Matthey Public Limited Company, London (GB)

( * ) Notice: Subject to any disclaimer, the term of this patent is extended or adjusted under 35 U.S.C. 154(b) by 203 days.

(21) Appl. No.: 10/221,766

(22) PCT Filed: Mar. 12, 2001

(86) PCT No.: PCT/GB01/01081

§ 371 (c)(1),
(2), (4) Date: Sep. 12, 2002

(87) PCT Pub. No.: WO01/68596

PCT Pub. Date: Sep. 20, 2001

(65) Prior Publication Data

US 2003/0118729 A1 Jun. 26, 2003

(30) Foreign Application Priority Data

Mar. 14, 2000 (GB) .............................. 0006050

(51) Int. Cl.[7] ................................ B05D 1/12
(52) U.S. Cl. ...................... 427/180; 427/216; 427/220
(58) Field of Search ................................ 427/212, 216, 427/220, 299, 301, 304, 402, 404, 180, 189, 190, 191

(56) References Cited

U.S. PATENT DOCUMENTS 2,490,399 A   12/1949   Ballard
3,163,665 A   12/1964   Fitch
3,245,809 A   4/1966    Fitch
5,639,901 A   6/1997    Schulz et al.
5,744,245 A   4/1998    Bishop
6,071,332 A * 6/2000    Schulz et al. ............. 106/31.01

FOREIGN PATENT DOCUMENTS

EP   0 514 073 A2   11/1992
EP   0 668 265 B1   8/1995
WO   WO 99/21934   5/1999

OTHER PUBLICATIONS

Johnson et al., "Influence of a Terminal Functionality on the Physical Properties of Surfactant–Stabilized Gold Nanoparticles," Langmuir 1998, 14, 6639–6647.*

Kiely et al., "Thin film structures formed from metallic nanoparticles; manipulation of the self–assembly process," Inst. Phys. Conf. Ser. No. 161: Section 10 (Electron Microscopy and Analysis) 1999, 515–520.*

Hao et al., "Buildup of Polymer/Au Nanoparticle Multilayer Thin Films Based on Hydrogen Bonding," Chem. Mater. 2000, 12, 3392–3396.*

Templeton et al., "Monolayer–Protected Cluster Molecules," Acc. Chem. Res. 2000, 33, 27–36.*

Boudnikoff, *Compt. Rend.*, 196 (1933), pp. 1898–1899 (w/ translation).

(Continued)

Primary Examiner—Shrive P. Beck
Assistant Examiner—William Phillip Fletcher, III
(74) Attorney, Agent, or Firm—RatnerPrestia (57) ABSTRACT

A method for decorating a substrate using novel thiol-stabilised gold nanoparticles of the general formula HSR where R is a $C_3$–$C_{60}$ alkyl group, aryl, benzyl, alicyclic, or heterocyclic group which is substituted or unsubstituted, branched or unbranched. The thiol-stabilised gold nanoparticles exhibit a plasmon frequency of between 480 and 600 nm.

16 Claims, 2 Drawing Sheets

OTHER PUBLICATIONS

Chemnitius, F., *J. Prakt. Chem.*, 117 (1927), pp. 245–261.

Nakatsuchi, A., *Journal of of the Society of Chemical Industry, Japan*; vol. 38, No. 11, pp. 617–619 Supp. 617B (1935).

Evans et al., "Vapour sensing using hybrid organic–inorganic nanostructured materials," *Journal of Materials Chemistry*, 2000, vol. 10, pp 183–188.

Schmid & Lehnen, "The Complexation of Gold Colloids", *Agnew. Chem. Int. Ed. Engl.* 28 (1989), No. 6 pp. 780–781.

M. Brust et al., "Synthesis of Thiol–derivatised Gold Nanoparticles in a Two–phase Liquid–Liquid System", *J. Chem. Soc.*, Chem. Comm., 1994, pp 801–802.

D. Bethell et al., "From Monolayers to nanostructured materials: an organic chemist's view of self–assembly", *Journal of Electroanalytical Chemistry*, 409, 1996, pp. 137–143.

UK Search Report for priority GB 0006050.9 application, dated Jul. 28, 2000.

Kiely et al., "Thin film structures formed from metallic nonoparticles; manipulation of the self–assembly process," Inst. Phys. Conf. Ser. No. 161, Sec. 10, (Electron Microscopy and Analysis) 1999, pp. 515–520.

Gutiérrez–Wing et al., "On the Structure and Formation of Self–Assembled Lattices of Gold Nanoparticles", *Journal of Cluster Science*, vol. 9, No. 4, 1998, pp 529–545.

Chen & Murray, Arenethiolate Monolayer–Protected Gold Clusters, *Langmuir*, vol. 15, 1999, pp. 682–689.

Chen et al., "Gold Nanoelectrodes of Varied Size: Transition to Molecule–Like Charging", *Science*, vol. 280, Jun. 28, 1998, pp. 2098–2191.

Maye et al., Heating–Induced Evolution of Thiolate–Encapsulated Gold Nanoparticles: A Strategy for Size and Shape Manipulations, *Langmuir*, 2000, vol. 16, pp. 490–497.

Bartz et al., Monothiols derived from glycols as agents for stabilizing gold colloids in water: systhesis, self–assembly and use as crystallization templates, *Jn. Mater. Chem.*, 1999, vol. 9, pp. 1121–1125.

International Search Report for PCT/GB01/01081, dated Aug. 7, 2001.

\* cited by examiner

METHOD OF DECORATING A SUBSTRATE BY APPLICATION OF GOLD NANOPARTICLES

The present invention relates to a novel gold material which confers advantageous characteristics upon compositions comprising said material. Uses and methods of the preparation of said material are also disclosed.

Liquid gold compositions have been known in the art and used for gilding and decorating substrates for a long time. Traditional liquid gold compositions contained gold sulpho-resinates in combination with natural resinous materials (by Boudnikoff, Compt. Rend., 196, 1898 (1933) and by Chemnitius, J. Prakt. Chem., 117, 245 (1927)). The gold sulpho-resinates are prepared by the reaction of a gold chloride solution with a sulphurised terpene. These are then diluted with natural oils such as lavender, rosemary and pine oils. Rosin and asphalt resins are added to thicken the compositions so that they are suitable for decorating, gilding or printing applications. Furthermore, small amounts of salts or resinates of metals such as rhodium, bismuth, chromium etc are also added as fluxes to these compositions to improve the lustre of the gold in the fired product and also to improve the adhesion of the gold applied to the substrate upon firing. In preparing other compositions, various gold mercaptides have been used. For instance, U.S. Pat. No. 2,490,399 describes the use of gold mercaptides of cyclic terpenes but does not provide any structure for the resultant mercaptide. Again, the mercaptide of gold prepared from thio-borneol has been described in the Journal of the Society of the Chemical Industry, Japan, 38, Supplement 617B (1935) by Nakatsuchi although this reference makes no mention of the possibility of using such compounds in decorating or gilding compositions. According to U.S. Pat. No. 3,163,665, the gold thiolates derived from cyclic terpenes have the disadvantage of requiring relatively high firing temperatures, thereby limiting their use on substrates such as glass, ceramics etc. and consequently recommends the use of non-terpenoid gold secondary mercaptides. Similarly, U.S. Pat. No. 3,245,809 claims and describes the use of a liquid gold decorating composition comprising a substituted gold aryl mercaptide wherein the sulphur is attached directly to the aryl nucleus which is already substituted by an alkyl group in solution in an organic vehicle and a gold flux. The specific aryl mercaptides disclosed include gold p-tert.-butylphenyl mercaptide prepared from p-tert.-butylbenzenethiol and aurous chloride.

Due to environmental awareness and potential legislative activity to remove hazardous organic materials from these organic based gold inks a series of water dilutable gold (1) thiolates have been produced as described in EP-A 0514 073. Additionally, EP 0668 265 describes the preparation and use of water soluble monogold (I) dithiolates for producing decorations on firable surfaces producing highly lustrous, pore free and spot and stain free decorations.

In U.S. Pat. No. 5,639,901 water soluble gold materials containing a gold content of 60–90% by weight and an atomic ratio of gold to sulphur of greater than 0.71 to 4:1 are described which are produced by a specific processing route using a monogold (I) dimercaptocarboxylic acid compound. Specific synthetic details involved adding acid to a solution of gold material to pH=2 or lower and then isolating the resultant material. There are problems with the use of these compounds however, for instance the water solubility of this gold material precludes their use in traditional water slide decalomania technology. Gold materials which do not dissolve in water are therefore required. This is the problem the present invention sets out to solve.

Nanoparticles have been known for decades. In the past five years the synthesis of nanoparticles with increased stability has been achieved (Schmidt and A. Lehnert, Angew. Chem. Int. Ed. Engl. 1989, 28, 780). For instance, thiol derivatised gold nanoparticles have been prepared by a two-phase reaction (Brust, M. Walker, D. Bethell, D. J. Shiffrin and C. Kiely, J. Chem. Soc. Chem. Commun., 1994, 801). These particles range from 1–10 nm and are made of a crystalline metallic core protected by a shell of ligands. This protecting shell prevents agglomeration by means of steric and electrostatic barriers and thus imparts a greater stability to these nanoparticles compared to those generated previously. They can also be isolated as dark solid materials and then redissolved in a wide range of solvents depending on the stabilisers forming the protective monolayer.

Metallic nanoparticles possess a characteristic plasmon resonance absorption (Creighton in *Surface Enhanced Raman Scattering* (Eds. R. K. Chang, T. E. Furtak), Plenum, New York 1982, 315–337.) A characteristic plasmon resonance absorption can also be observed for stabilised nanoparticles. This surface plasmon phenomenon is a collective excitation of free electrons at the interface between a metallic core and the insulating shell of ligands. In the case of small nanoparticles, the plasmon resonance absorption can often be very weak as reported by Brust et al. (Bethell, M Brust, D. J. Schriffin and C. Kiely, J. Electroanalytical Chem., 1996, 409, 137–143).

The present invention provides a water insoluble gold material designed specifically for decorative uses comprising gold nanoparticles stabilised by thiol ligands. In the material the gold forms a central metallic core which is stabilised by thiol groups. This new group of gold materials possess a number of advantages over those gold compounds previously described:

The majority of known gold (I) thiolate compounds used for decorative purposes exhibit poor solubility in common organic solvents. This poor solubility precludes the use of many know gold (I) thiolate compounds (without further modification) in traditional organic liquid gold formulations. A limited number of sterically hindered compounds which show high organic solubility such as $AuS\text{-}t\text{-}C_{12}H_{25}$, $AuS\text{-}t\text{-}C_9H_{19}$, $AuSCHMeC_6H_5$, $AuSC_6H_4\text{-}pCMe_3$ have been patented (U.S. Pat. No. 889,912, U.S. Pat. No. 3,163,665, U.S. Pat. No. 3,245,809) for use in liquid gold formulations. The gold nanoparticles of the present invention have been found to show a significant increase in solubility over their molecular gold thlolate analogues. This increase in solubility means that the formulator has a significantly increased choice of thiol that can be used to stabilise the gold nanoparticles in compositions. The formulator also has a significant increase in the choice of solvents available for dissolution of the gold nanoparticles, ranging from the traditional non-polar organic solvents through to more polar, and importantly, less harmful glycol ether type solvents which are increasingly being used in the formulations industry.

They can be used in the production of decalomanlas: The phenomenon of bleeding and purple discolouration is significantly reduced when the gold composition of the present invention is used compared with their molecular gold thiolate analogue.

Nanoparticles of the present invention form a stable metallic film when applied to a substrate surface followed by heating from as low as 100° C. to as high as 1200° C. In addition, metallic films can be produced without heating, i.e., a metallic film can be produced without firing, by performing an appropriate post-treatment on a solvent cast film. Examples of post-treatments may include washing with acid and irradiating with UV light. This makes a gold composition of the present invention particularly suitable for use on non firable substrates such as plastic and paper.

In a first aspect the present invention provides the use of a gold material for decorative purposes characterised in that said material comprises gold nanoparticles stabilised by thiol groups described by the general formula shown below, said compound exhibiting a plasmon frequency of between 480 and 600 nm:

HSR

Where:

R=is a C3–C60 alkyl group, aryl, benzyl or alicyclic or heterocyclic group which may be substituted or unsubstituted, branched or unbranched.

In a preferred embodiment of the invention R is a C3–C30 alkyl group, aryl, benzyl or alicyclic or heterocyclic group which may be branched or unbranched substituted or unsubstituted. The substitution groups are preferably carboxylate groups, esters, thioethers, ethers, amines, hydroxy amines and/or amides.

Where R is an alkyl group, then preferably the substituted groups are any one or more of the following:

—C(O)—OR" where R" is $C_1$–$C_{-15}$ alkyl which may be branched or unbranched, —C—O—R" or C—S—R" where R" is $C_1$–$C_{-15}$ alkyl which may be branched or unbranched, —C—NR'R" where R' and/or R"=H or is $C_1$–$C_{-15}$ alkyl which may be branched or unbranched, —C(O)—N—R'R" where R' and/or R"=H or is $C_1$–$C_{-15}$ alkyl which may be branched or unbranched, —aryl group —SH group In an alternative embodiment R is aryl. Preferably, the aryl group is benzene, which may be substituted in any one or more positions around the ring structure or may be unsubstituted. The substituents may be but are not limited to C1–C15 alkyl, groups aryl, benzyl, alicyclic or heterocyclic groups which may be branched or unbranched. Where the substituents are C1–C15 alkyl groups they may be substituted as herein described for the case where R is an alkyl group.

In a preferred embodiment R is a benzyl group in which the aromatic moiety may be substituted in any one or more positions around the ring structure or may be unsubstituted. The substituents may be, but are not limited to C1–C15 alkyl groups, aryl, benzyl, alicyclic or heterocyclic groups which may be branched or unbranched. Where the substituents are C1–C15 alkyl groups they may be substituted as herein described for the case where R is an alkyl group. Alternatively or in addition the benzylic carbon may be branched or unbranched, unsubstituted or substituted as herein described for the case where R is alkyl.

In a further embodiment R is a nitrogen, phosporous, sulphur or oxygen containing heterocycle group in which the thio group is attached to a carbon group within said heterocycle ring structure.

Suitable thiol groups for use in a nanoparticle preparation used in the present invention include but are not limited to: $HSC_6H_5$, $HSC_6H_4$-p-$CMe_3$, $HSC_6H_4$-o-$CMe_3$, $HSC_6H_3$-2-$CMe_3$-4-$CMe_3$, $HSC_6H_3$-2-$CH_3$-5-$CMe_3$, $HSC_6H_4$-2-$CH_3$-4-$CMe_3$, $HSC_6H_4$-o-$CH_3$, $HSC_6H_4$-o-$C_2H_5$, $HSC_6H_4$-p-$CH_3$, $HSC_6H_4$-p-$C_2H_5$, $HSC_6H_4$-o-$C_3H_7$, $HSC_6H_4$-p-$C_3H_7$, $HSC_6H_4$-o-$OCH_3$, $HSC_6H_4$-p-$OCH_3$, $HSC_6H_4$-p-OH, $HSC_6H_4$-p-$NHCOCH_3$, $HSC_6H_3$-3-$CH_3$-5-$CH_3$, HS-pinanyl, $HSCH_2CO_2C_8H_{17}$, $HSCH_2CO_2CH_3$, $HSCH_2CO_2C_2H_5$, $HSCH_2CO_2C_4H_9$, $HSCHMeCO_2CH_3$, $HSCHMeCO_2C_2H_5$, $HSCMe_2CH_2NH_2$, $HSC_2N_2S$—SH, $HSC_6H_{11}$, $HSC_{10}H_7$, $HSCH_2C_6H_5$, $HSCHMeC_6H_5$, $HSCH_2C_6H_2$-2-$CH_3$-4-$CH_3$-6-$CH_3$, $HSC_6H_4$-o-$CO_2Me$, $HSC_{12}H_{25}$, $HSC_9H_{19}$ $HS(CH_2)_9SH$, $HSC_6H_4$-2-SH, $HSC_6H_4$-3-SH.

Nanoparticles defined in the present invention are specifically designed for decorative uses. They may be applied alone to the substrate surface, in powder or in liquid form. Alternatively they may be applied to the substrate surface in the form of a preparation comprising them.

In a further aspect, the present invention provides a gold material suitable for decorative purposes which is described by the general formula described herein and is $HSC_6H_4$-$pCMe_3$ where H is hydrogen, S is sulphur, C is carbon, Me is methyl.

In another aspect, the present invention provides a gold material suitable for decorative purposes which is described by the general formula described herein and is H S pinanyl In another aspect, the present invention provides a gold material suitable for decorative purposes, which is described by the general formula herein and is $HS(CH_2)_{11}CH_3$ In another aspect, the present invention provides a gold material suitable for decorative purposes, which is described by the general formula herein and is $HSCH(Me)CO_2CH_2CH_3$ Thus, in a further aspect, the present invention provides a composition comprising gold material as herein described and at least one solvent.

Typically a composition of the present invention will comprise 0.01% to 50% by weight of gold. The selection of suitable solvents will be dependent on the chemical composition of the thiol ligand chosen to stabilise the gold nanoparticle. Properties such as solvent viscosity, evaporation rate and surface tension will also need to be considered, dependent on the manner in which the composition is to be applied to the substrate. Suitable solvents include but are not limited to aldehydes, alcohols, ketones, aliphatic hydrocarbons, aromatic hydrocarbons, alkyl acetates, glycol ethers, terpenes, natural oils and waxes.

More specifically, these may include one or more of the following: methyl ethyl ketone, cyclohexanone, isophorone, ethyl acetate, ethyl lactate, butyl lactate, amyl acetate, cyclohexanol, propylene glycol butyl ether, propylene glycol phenyl ether, dipropylene glycol dimethyl ether, dipropylene glycol methyl ether, propylene glycol methyl ether acetate, toluene, xylene, terpenes such as pinene, dipentene oxide, natural oils such as lavender, rosemary oil, citronellol, fenchone, cyclohexylethanol, trimethylcyclohexanone, alkyldimethoxy benzene.

Furthermore, the addition of non-polymeric solids, for example camphor, tert-butyl cyclohexanone, cyclohexanedimethanol, isomenthol may be beneficial to the composition, as they act as solvents for the gold nanoparticles during the firing process.

The composition may additionally comprise minor metal additives. These are small amounts of metal salts, compounds or resinates which are present in the composition to improve the adhesion of the gold metallic film onto the substrate on firing by formation of metal oxides. Careful selection of minor-metal additives in the composition, dependent on the substrate used, will enable the achievement of good chemical and abrasion resistance. They are also used to influence the fired colour of the gold film.

Suitable minor metal additives include but are not limited to salts, compounds or resinates of antimony, bismuth, boron, cerium, chromium, cobalt, copper, iridium, rhodium, silicon, silver, tin, titanium, vanadium, palladium, platinum, zirconium, selenium, indium. The amount of minor-metal additives added to the compositions is suitably in the range from about 0.01 to 10% by weight, preferably from about 0.05 to 5.0% by weight. Percentage is the total amount of minor metal additives in the present invention.

The composition may additionally comprise at least one polymer or mixture of polymers. The function of such polymers is to alter the viscosity and viscoelastic nature of the composition such that the composition can be applied to the substrate. A further function of the polymer is to provide green strength to the applied composition, before it undergoes heat treatment to produce the metallic film. A further function can be to protect the gold nanoparticles from attack by the organic solvents when the gold containing film is overprinted with commercially available covercoats as part of the decalomania production process. With careful selection of the polymer or mixture of polymers the bleeding and purple discolouration that can be observed on firing conventional gold inks suitable for decalomania is significantly reduced or eliminated. One skilled in the art will appreciate that it is the particular combination of polymer with gold material which is crucial. For example Scripset 540 resin and p-t-butylthiophenol ($HSC_6H_4$-$pCMe_3$) stabilised nanoparticles produce particularly favourable results. Examples of polymers which can be used include, poly(acrylates), poly(methacrylates), polycarbonates, cellulose derivatives, poly(styrene-co-maleic anhydride) polymers both partially esterified and non-esterified, poly(vinylpyrrolidone), poly(styrenes), poly(ketones), poly(vinylalcohols), poly(vinylacetates), poly(vinylbutyral), poly(esters), polyurethanes.

In addition, rosin derived materials such as hydrogenated rosins, rosin dimers, maleated rosin, and rosin esters, and their sulphided derivitives, may additionally be used and can be combined with the above polymers.

Additional materials which may be added to compositions are surfactants such as poly(siloxane) based wetting agents; viscosity modifiers, such as hydrogenated castor oils; matting agents such as micas and talcs; and pigments, dyes, frits, precious metal flakes and powders.

In a further aspect the present invention provides a method for the production of gold material as herein described comprising the steps of:

Transferring an aqueous gold source into an organic layer using a phase transfer agent.

Admixing said gold source with thiol groups and then.

Reducing the resultant mixture to produce stabilised nanoparticles.

A standard method has been developed by the present inventors which overcomes many of the problems with the method previously known in the art. Additionally, it provides some surprising advantages over the methods previously used. A detailed description of the procedure is detailed in example 1. The nanoparticles typically are characterised by an assay of 78.2±1.0% but this can be increased or decreased by varying the reaction conditions. Factors influencing the gold assay of the particles include variation of molar ratios, temperature, addition rates, concentration and reaction time.

The method of the present invention is a modification of a method described by Brust, M. Walker, D. Bethell, D. J. Shiffrin and C. Kiely, *J. Chem. Soc. Chem. Commun.*, 1994, 801 which was found to have the following problems:

On a large scale basis, the literature method causes foaming which is very difficult to control.

On a large scale basis the same method causes a large increase in temperature, which is also difficult to control.

Both of these problems preclude the use of this method for large scale preparations of nanoparticles. The present inventors have found, however, if one of the steps is reversed: that is the organic phase mixture for example $AuCl_4^-$/ammonium salt/thiol is added to the reducing agent, then surprisingly the problems of the prior art are overcome.

Preferably, the phase transfer reagent is an ammonium salt with long alkyl chains (for instance, aliquat®336-[$CH_3(CH_2)_7$]$_3NCH_3^+Cl^-$, adogen®336-[$CH_3(CH_2)_n$]$_3NCH_3^+Cl^-$ with n=8–10, or [$CH_3(CH_2)_n$]$_4N^+X^-$ with n=5–12 and X=halogen, $NO_3^-$, $HSO_4^-$). Preferably the reducing agent is an aqueous solution of sodium borohydride. Other suitable reducing agents include but are not limited to aluminum hydrides of the type $R_2AlH$, $RAlH_2$, $ER_3AlH$ with E=Li or Na and R=alkyl group (e.g. $LiAlH_4$ or $LiAl[OC(Me)_3]_3H$); borane derivatives of the type $EBH_{4-n}L_n$ where n=0–4, E=organic cation, tetra-ammonium cations, Na, Li and K and L=alkyl, alkoxy, amine, amide, phosphine etc. (e.g. [$CH_3(CH_2)_3$]$_4NBH_3CN$ or $NaB[OOCMe]_3H$).

The present inventors have found that of particular importance when performing this method is the $AuCl_4^-$/thiol ratio to control the gold assay. Generally it is found that the solubility and thus stability of the stabilised gold nanoparticles decrease with increasing gold assay.

Gold nanoparticles of the present invention can also be reacted with molecular silver compounds such as silver thiolates, silver dithiocarbamates, silver nitrate and silver carboxylates. The reaction simply involves heating and stirring of the two components in a suitable organic solvent such as toluene. The incorporation of the molecular silver compounds results in the agglomeration of the individual gold nanoparticles into larger particles, presumably by interactions between silver and a lone pair of electrons available on the thiol stabilising the gold nanoparticles. This increase in agglomeration is reflected by a change in colour of the nanoparticles in solution from brown (gold only) to purple-red (gold and silver). An increase in the intensity of the surface plasmon band is also clearly evident in the uv-visible spectra, again indicating an increase in nanoparticle size.

The gold-silver materials obtained can be used for decorative purposes as for the gold nanoparticles, but with the attainment of what is known to those skilled in the art as a lemon gold film after firing.

Once the nanoparticles have been prepared using the method herein described, they can be applied to a substrate surface for decorative uses.

Thus, in a further aspect, the present invention provides a method for decorating a substrate surface, said method comprising the steps of applying a gold material or gold composition as herein described to a substrate surface and treating said substrate to adhere said gold material or gold composition to the substrate surface to produce a decorative effect. According to another exemplary embodiment of the present invention, the step of treating the substrate to adhere the gold material to the substrate does not involve firing.

Suitable treatments include but are not limited to heating from as low as 100° C. to as high as 1200° C. Additionally performing an appropriate post-treatment on a solvent cast film, for example washing with acid and/or irradiating with UV light produces metallic films exhibiting a decorative effect.

The substrate may be but is not limited to any one or more of the following: glass, earthenware, bone china, porcelain, silicate materials, metals, quartz, carbon, mica, plastics, laminates, wood, paper, textiles and leather. The firing temperature used will depend to some extent on the composition of the formulation containing the nanoparticles, but more importantly it will depend on the substrate surface upon which the decoration is applied. Low temperatures (<300° C.) are required for firing onto plastics, laminates, wood, paper and leather. Temperatures of 400 to 700° C. are typically used for firing of gold films onto glass, whilst firing onto bone china or porcelain involves firing temperatures between 700 and 1100° C., typically between 700 and 900° C. In addition a combination of the gold material or gold composition with special sintering agents may be required for the high temperature applications.

The gold material or gold composition of the present invention may be applied onto the substrate by any one or more of the following methods: brush coating, ink-jet printing, stencilling, spraying, stipling, screen printing, spin coating, curtain coating, dip coating, pad printing, thermoplastic printing, wheel banding, decalomania, or electrostatic printing.

In the case that the method of application to the substrate is by decalomania it is found that the resultant decalomania exhibits minimal surface bleeding when compared with the molecular gold thiolate analogue.

The invention will now be described by the following examples in which:

FIG. 1: (a) Shows a transmission electron micrograph of gold nanoparticles produced according to example 1 of the present invention. (b) The particle size distribution of nanoparticles produced according to example 1. The vertical axis shows the percentage of particles and the horizontal axis shows the average diameter of the particles in nm.

EXAMPLES

Figure 1A:
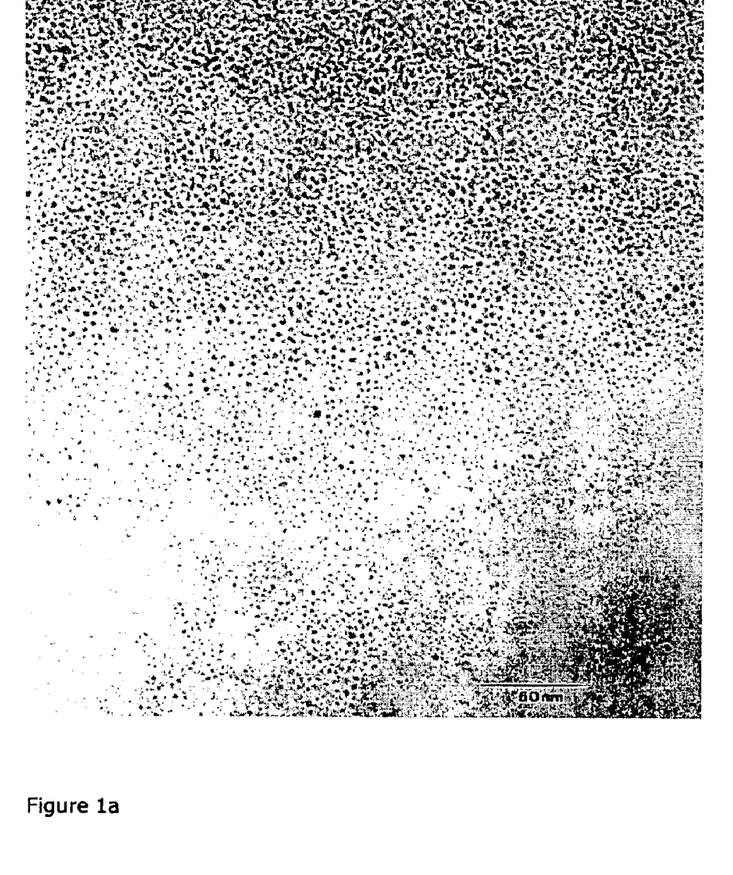
Figure 1B:
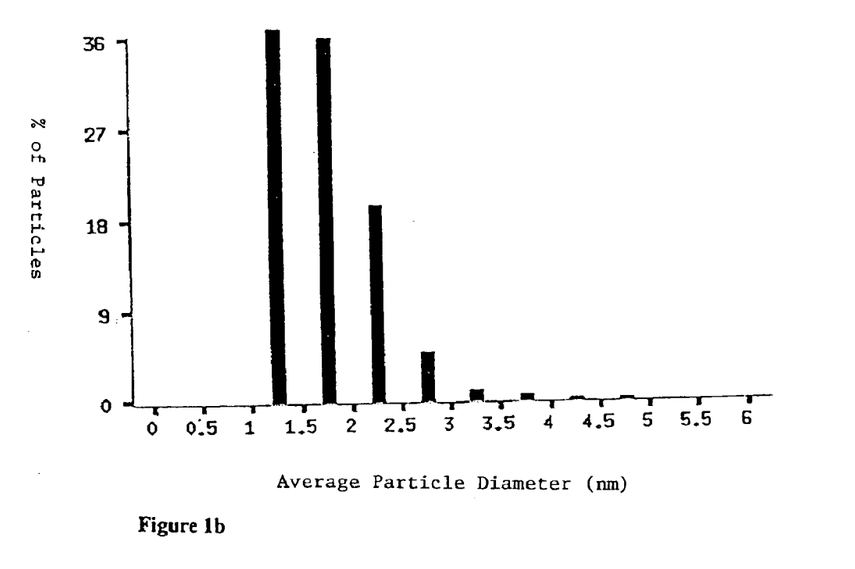

Example 1
General Procedure for the Preparation of Thiol Stabilised Gold Nanoparticles A 600 cm3 aqueous solution of $HAuCl_4$ (50 g, 0.1057 moles) was mixed with a 600 cm3 toluene solution of the phase transfer reagent, aliquat®336 (170.9 g, 0.4228 moles). The two-phase system was stirred at room temperature until complete transfer of the anion $AuCl_4^-$, i.e. colourless aqueous phase. The orange organic phase was then isolated and washed twice with an appropriate amount of water. On addition of $HSC_6H_4$-p-$CMe_3$ (35.08 g, 0.2113 moles), the mixture turned green and finally orange within 15 min. The mixture was added to a freshly prepared 2000 cm3 solution of sodium borohydride (79.96 g, 2.113 moles) with vigorous stirring while the reaction was cooled in a water bath to keep the reaction temperature below 40° C. during addition. A dark brown organic layer was instantly obtained and further stirring at room temperature was allowed for 15 min after addition. The organic phase was separated and washed twice with an appropriate amount of water. Addition of large volumes of methanol led to precipitation of a black powder, which was isolated by filtration, washed with methanol and recrytallised from toluene/MeOH.

It is found that subtleties in the reaction conditions can result in an variation of up to +/−1.0% in the gold assay when repeating the same procedure.

Product Characteristics
 Colour: black powder
 Yield: 87%
 Au assay: 78.2%
 Elemental analysis: C, 16.00; H, 1.88; S, 4.31;
 Particle size (nm): The majority are between 1 and 2.5 nm
 TGA analysis: exotherm at 223° C.
 UV-vis spectrum: surface plasmon at 500 nm
 1H NMR spectrum: broad resonances (br) with shift given at the centre, 1.1 (br, 9H) and 7.2 (s, 4H) ppm

Example 2
Preparation of Thiol Stabilised Nanoparticles

As for example 1 with the following quantities: $HAuCl_4$ (50 g, 0.1057 moles), aliquat®336 (58 g, 0.143 moles). $HSC_6H_5$-p-$CMe_3$ (17.54 g, 0.1057 moles) and $NaBH_4$ (20 g, 0.528 moles). The two-phase system involved; 200 ml of toluene was used for the organic phase to mix $AuCl_4^-$, aliquat®336 and $HSC_6H_5$-p-$CMe_3$ and $NaBH_4$ was dissolved in 500 ml of demineralised $H_2O$ to form the aqueous phase.

Product characteristics
 Colour: black powder
 Yield: 86%
 Au assay: 77.5%
 Elemental analysis: C, 16.06; H, 1.7; S, 4.2;
 TGA analysis: exotherms at 218.05 and 276.8° C.
 UV-vis spectrum: surface plasmon at 500 nm
 1H NMR spectrum: broad resonances with shift given at the centre, 1.1 (s, 9H) and 7.2 (s, 4H) ppm.

Example 3
Preparation of Thiol Stabilised Nanoparticles

As for the general procedure with the following quantities: $HAuCl_4$ (50 g, 0.1057 moles), aliquat®336 (58 g, 0.143 moles), $HSC_6H_5$-p-$CMe_3$ (8.77 g, 0.0528 moles) and $NaBH_4$ (20 g, 0.528 moles). The two-phase system involved: 200 ml of toluene was used for the organic phase to mix $AuCl_4^-$, aliquat®336 and $HSC_6H_5$-p-$CMe_3$ and $NaBH_4$ was dissolved in 500 ml of demineralised $H_2O$ to form the aqueous phase.

Product Characteristics
 Colour: black powder
 Yield: 88%
 Au assay: 81%
 Elemental analysis: C, 13.53; H, 1.03; S. 3.8;
 TGA analysis: exotherm at 223° C.
 UV-vis spectrum: surface plasmon at 500 nm
 1H NMR spectrum: broad resonances with shift given at the centre, 1.1 (s, 9H) and 7.2 (s, 4H) ppm.

Example 4
Preparation of Thiol Stabilised Nanoparticles

As for the general procedure with the following quantities: $HAuCl_4$ (50 g, 0.1057 moles), aliquat®336 (58 g, 0.143 moles), $HSC_6H_5$-p-$CMe_3$ (8 g, 0.048 moles) and $NaBH_4$ (20 g, 0.528 moles). The two-phase system involved: 200 ml of toluene was used for the organic phase to mix $AuCl_4^-$, aliquat®336 and $HSC_6H_5$-p-$CMe_3$ and $NaBH_4$ was dissolved in 500 ml of demineralised $H_2O$ to form the aqueous phase.

Product Characteristics
 Colour: black powder
 Yield: 91%
 Au assay: 83%
 Elemental analysis: C, 12.2; H, 1; S, 3.64;
 TGA analysis: exotherm at 220° C.
 UV-vis spectrum: surface plasmon at 500 nm
 1H NMR spectrum: broad resonances with shift given at the centre, 1.1 (s, 9H) and 7.2 (s, 4H) ppm.

Example 5
Preparation of Thiol Stabilised Nanoparticles

Method as for the general procedure using the following quantities: $HAuCl_4$ (40 g, 0.0846 moles), aliquat®336 (34.2 g, 0.169 moles), $HSC_6H_5$-p-$CMe_3$ (3.5 g, 0.0211 moles) and $NaBH_4$ (32 g, 0.846 moles). The two-phase system involved: 240 ml of toluene was used for the organic phase to mix $AuCl_4^-$, aliquat®336 and $HSC_6H_5$-p-$CMe_3$ and $NaBH_4$ was dissolved in 800 ml of demineralised $H_2O$ to form the aqueous phase.

Product Characteristics
 Colour: black powder
 Yield: 90%
 Au assay: 91%
 Elemental analysis: C, 6.6; H, 0.42; S, 2;
 TGA analysis: exotherm at 233° C.
 UV-vis spectrum: surface plasmon at 500 nm 1H NMR spectrum: broad resonances with shift given at the centre, 1.1 (s, 9H) and 7.2 (s, 4H) ppm.

Example 6
Preparation of Thiol Stabilised Nanoparticles

Method as for the general procedure using the following quantities: $HAuCl_4$ (50 g, 0.1057 moles), aliquat®336 (58 g, 0.143 moles), $HSC_6H_5$-p-$CMe_3$ (8.77 g, 0.053 moles) and $NaBH_4$ (20 g, 0.528 moles). The two-phase system involved: 200 ml of xylene was used for the organic phase to mix $AuCl_4^-$, aliquat®336 and $HSC_6H_5$-p-$CMe_3$ and $NaBH_4$ was dissolved in 500 ml of demineralised $H_2O$ to form the aqueous phase.

Product Characteristics
 Colour: black powder
 Yield: 92%
 Au assay: 79.5%
 Elemental analysis: C. 14.97; H. 1.6; S, 3.29;
 TGA analysis: exotherm at 222° C.
 UV-vis spectrum: surface plasmon at 500 nm
 1H NMR spectrum: broad resonances with shift given at the centre, 1.1 (s. 9H) and 7.2 (s, 4H) ppm.

Example 7
Preparation of Thiol Stabilised Nanoparticles

To a 20 cm3 toluene solution of $[CH_3(CH_2)_7]_4N^+Br^-$ (20.6 g, 0.037 moles). $HAuCl_4$ diluted in 50 cm3 demineralised water (5 g, 0.0105 moles) was added to allow phase transfer of $AuCl_{-4}^-$ into the organic layer. Subsequently, the thiol HSpinanyl (2.98 g, 0.037 moles) was added and the mixture stirred for 15 mins. Finally 20 cm3 of a freshly prepared $NaBH_4$ aqueous solution (3.78 g, 0.100 moles) was added dropwise to give a dark brown mixture which was stirred at room temperature for 3 hours after addition. The organic layer was then isolated and concentrated under vacuum. Ethanol was added and the mixture was stored at −15° C. for 48 hours. A dark solid was obtained, filtered and washed with MeOH. The black material was finally dried under vacuum for 24 hours.

Product Characteristics
 Colour: black powder
 Yield: 86%
 Au assay: 78.6%
 Elemental analysis: C. 14.55; H. 1.92; S, 4.44

Example 8
Preparation of Thiol Stabilised Nanoparticles

As for example 1 but using the following quantities: $HAuCl_4$ (0.849 g, 0.9 mmoles), $[CH_3(CH_2)_7]_4N^+Br^-$ (4.37 g, 4 mmoles). $HS(CH_2)_{11}CH_3$ (0.34 g, 1.68 mmoles) and $NaBH_4$ (0.756 g, 0.010 moles).

Product Characteristics
 Colour: black powder
 Yield: 86%
 Au assay:73.5%
 Elemental analysis: C. 18.74; H. 13.28; S., 4.58

Example 9
Preparation of Thiol Stabilised Nanoparticles

A 200 cm3 aqueous solution of $HAuCl_4$ (25 g, 0.0529 moles) was mixed with a 250 ml toluene solution of the phase transfer reagent, aliquat®336 (79.07 g, 0.195 moles). The two-phase system was stirred at room temperature until complete transfer of the anion $AuCl_4^-$, i.e. colourless aqueous phase. On addition of $HSCH(Me)CO_2CH_2CH_3$ (12.78 g, 0.095 moles), the mixture turned green and finally orange within 15 min. This was added to a freshly prepared 200 cm3 solution of sodium borohydride (79.96 g, 2.113 moles) with vigorous stirring while the reaction was cooled in a water bath to keep the reaction temperature below 40° C. during addition. A dark purple organic layer was instantly obtained and further stirring at room temperature was allowed for 6 hours after addition. The organic layer was then isolated and concentrated under vacuum. MeOH was added and the mixture was stored at −15° C. for 48 hours. A dark solid was obtained, filtered and washed with MeOH. The black material was finally dried under vacuum for 24 hours.

Product Characteristics
 Colour: black powder
 Yield: 80%
 Au assay: 89%

Example 10
General Preparative Route for the Reaction of Gold Nanoparticles (Prepared as Example 1) with Silver Compounds Gold nanoparticles (as for example 1, assay 78.5%) were dissolved in a suitable organic solvent and stirred. The desired silver compound was added to the reaction vessel (typically in a molar ratio of 1:0.2 Au:Ag) and the reaction was stirred and heated to 60° C. for 30 minutes, before being allowed to cool to room temperature. A visible colour change from brown to red-purple was observed, in keeping with an increase in colloidal size. The solution was then filtered to remove any small amounts of insoluble material before evaporation of the reaction solvent. The dried material was either washed with, or recrystallised from a suitable solvent, filtered and dried.

Example 11
Reaction of Gold Nano-particles with Silver Nitrate

The reaction was carried out according to the above general procedure using the following reagents:

| | |
|---|---|
| Gold nanoparticles (as example 1) Assay 78.5% | 5.0 g, (3.92 g Au, 0.02 moles) |
| Silver Nitrate | 0.616 g, (0.392 g Ag, 0.0036 moles) |
| Solvents- Reaction | Toluene (20 cm3)/Ethanol (20 cm3) |
| Washing | Water (100 cm3) |

Example 12
Reaction of Gold Nano-particles with AgSC6H4-p-CMe3

The reaction was carried out according to the above general procedure using the following reagents:

| | |
|---|---|
| Gold nanoparticles (as example 1) Assay 78.5% | 10.0 g, (7.85 g Au, 0.04 moles) |
| AgSC6H4-p-CMe 3 | 1.99 g, (0.785 g Ag, 0.0073 moles) |
| Solvent- Reaction | Xylene (50 cm3) |
| Washing | Methanol (100 cm3) |

Example 13
Reaction of Gold Nano-particles with AgSC6H4-p-CMe3

The reaction was carried out according to the above general procedure using the following reagents:

| | |
|---|---|
| Gold nanoparticles (as example 1) Assay 78.5% | 10.0 g, (7.85 g Au, 0.04 moles) |
| AgSC6H4-p-CMe3 | 1.49 g, (0.59 g Ag, 0.0055 moles) |
| Solvent- Reaction | Xylene (50 cm3) |
| Washing | Methanol (100 cm3) |

The products from the reactions were characterised by their assay, uv-visible spectra and 1H NMR spectra

|  | Example 11 | Example 12 | Example 13 |
|---|---|---|---|
| Assay (theoretical) | 77.9 (80.0) | 72.3 (72.0) | 73.4 (73.4) |
| Surface Plasmon Band Position | Broad band at ~520 nm | Broad band at ~540 nm | Broad band at ~540 nm |
| 1H NMR | As for example 1 | As for example1, but with sharp resonances at 1.2, 1.3 ppm and sharp multiplets in the aromatic region. | As for example1, but with sharp resonances at 1.2, 1.3 ppm and sharp multiplets in the aromatic region. |

Compositions Demonstrating the Use of Nanoparticles

The compositions were prepared by the combination of the thiol stabilised gold nanoparticles with the solvents and resins, followed by the addition of the minor-metal additives. Adequate heating and stirring was carried out to ensure the attainment of smooth homogenous compositions. Formulations were left to stand overnight, and then printed through a 120T mesh polyester screen (unless otherwise stated in the examples). Prints were covercoated with OPL500 thix (available from Johnson Matthey Colours and Coatings Division) after drying for a minimum of 3 hours. Once dry, the transfers were applied to bone china and porcelain ware. The compositions were assessed for fired film quality by firing to 840° C. over 1 hour cold to cold.

All compositional data is in % by weight, with the gold nanoparticle % adjusted to give an approximate concentration of 10 wt % Au in the formulation. The trade names Scripset 540 and Scripset 550 are poly(styrene-co-maleic acid), partial butyl ester resins of molecular weight 180,000 and 105,000 respectively. They are commercially available from Hercules Inc. The vanadium prep and chromium nuosyn 5 are available from Johnson Matthey Colours and Coatings Division.

Example 14
Gold Nano-particle Containing Composition

| | |
|---|---|
| 12.8 | Gold nanoparticles (as from example 1) |
| 4.8 | Silver sulphoresinate (21% silver) |
| 3.0 | Rhodium ethyl hexanoate solution (10 wt % in cyclohexanone) |
| 1.5 | MeSi(OEt)3 solution (5 wt % in cyclohexanone) |
| 1.0 | Vanadium prep |
| 1.0 | Chromium nuosyn 5 |
| 40 | Scripset 540 solution (40 wt % in dipropylene glycol dimethyl ether) |
| 10 | Scripset 550 solution (30 wt % in cyclohexanone) |
| 15 | Propylene glycol phenyl ether |
| 10.9 | 4-tert-butyl cyclohexanone |

The formulation gave fired films that were virtually free of bleeding under the covercoat. Abrasion resistance and chemical durability was comparable to current, commercially available products.

Example 15
Gold Nano-particle Containing Composition

| | |
|---|---|
| 12.6 | Gold nanoparticles of assay 79.5% (prepared as for example 6) |
| 50 | Scripset 540 solution (40 wt % in dipropylene glycol dimethyl ether) |
| 17.5 | Ethyl lactate |
| 6 | Camphor |
| 6 | 4-t-butylcyclohexanone |
| 2.4 | Silver sulphoresinate (21% Ag) |
| 3 | Rh ethyl hexanoate (10% solution in cyclohexanone) |
| 2.4 | (EtO)3SiMe (5% solution in cyclohexanone) |
| 0.1 | Byketol Special |

The resultant gold film was bright and smooth with minimal covercoat interaction.

Example 16

Gold Nano-particle Containing Composition

| | |
|---|---|
| 15.2 | Gold nanoparticles reacted with silver nitrate (as example 11) |
| 2 | Rhodium ethyl hexanoate solution (10 wt % in cyclohexanone) |
| 1.5 | MeSi(OEt)3 solution (5 wt % in cyclohexanone) |
| 1.0 | Vanadium prep |
| 1.0 | Chromium nuosyn 5 |
| 25 | Scripset 540 solution (40 wt % in dipropylene glycol dimethyl ether) |
| 25 | Scripset 540 solution (40 wt % in dipropylene glycol methyl ether) |
| 10.3 | Propylene glycol phenyl ether |
| 5 | Isophorone |
| 7 | 4-tert-butyl cyclohexanone |
| 7 | Camphor |

The resultant gold film was bright and smooth with slight purpling at the edges of the print.

Example 17

Brushing Formulation

| | |
|---|---|
| 12.8 | Gold nanoparticles (as for example 1) |
| 4.8 | Silver sulphoresinate (21% silver) |
| 3.0 | Rhodium ethyl hexanoate solution (10 wt % in cyclohexanone) |
| 1.5 | MeSi(Oet)3 solution (5% wt in cyclohexanone) |
| 20 | Scripset 540 solution (40 wt % in cyclohexanone) |
| 40 | Cyclohexanone |
| 17.9 | Alpha pinene |

Example 18

Formulation Suitable for Brushing or Spinning

| | |
|---|---|
| 12.7 | Gold nanoparticles (as for example 1) |
| 75.5 | Dipropylene glycol dimethyl ether |
| 8.4 | Co-polymethacrylate resin, DRM-99095 (available from Lawter International) |
| 3.4 | Rhodium ethyl hexanoate (10 wt % in cyclohexanone) |

The formulation was spun onto a porcelain tile and fired to 840° C. over a one hour cycle. The resulting film was a bright, reflective gold.

Example 19
Formulation Suitable for Dip Coating

Formulation with Au nanoparticles stabilised with ethyl 2-mercaptopropionate

| | |
|---|---|
| 37.5 | Gold nanoparticles (assay 89% Au, prepared as example 9) |
| 62.5 | Isophorone |

The composition was dip coated onto a thin sheet of polyester (as used for overhead projectors) and warmed to ca. 100° C. A bright gold film was formed.

Example 20
Gold Nano-particle Containing Composition

| | |
|---|---|
| 12.7 | Gold nano-particles of assay 78.0% |
| 47.9 | Scripset 540 solution (40 wt % in diproplylene glycol dimethyl ether) |
| 20 | Citronellol |
| 6 | 4-t-butylcyclohexanone |
| 6 | Camphor |
| 1.4 | Silver sulporesinate (21% Ag) |
| 2 | Rh ethyl hexanoate (10% solution in cyclohexanone) |
| 2 | Byk 141 |

Example 21
Gold Nano-particle Containing Composition

| | |
|---|---|
| 1.9 | Gold nano-particles of assay 78.0% |
| 1.1 | Poly(styrene-co-maleic acid) partial isobutyl ester with average Mw of 65 000 (50 wt % in dipropylene glycol dimethyl ether) |
| 1.8 | Citronellol |
| 1.8 | Thixcin R |
| 1.4 | Silver sulphoresinate (21% Ag) |
| 2 | Rh ethyl hexanoate (10% solution in cyclohexanone) |
| 0 | Vanadium Prep (50 wt % solution in xylene) |
| 1 | Chromium Prep (50 wt % solution in xylene) |
| 2 | Byk 141 |

The resultant gold film was bright with no covercoat interation.

COMPARATIVE EXAMPLES

Comparable Example with Molecular Gold Thiolate

| | |
|---|---|
| 18.3 | AuSC6H 4-p-CMe3 |
| 50 | Scripset 540 solution (30 wt % cyclohexanone) |
| 2 | Rhodium ethyl hexanoate solution (10 wt % cyclohexanone) |
| 0.2 | Triphenyl bismuth |
| 29.5 | Isophorone |

Formulations gave fired films (from decalomanias) which showed covercoat interaction with purpling around the edge of the print, and a surface scum on the gold. This scum can be removed to leave a bright gold film, but the purpling can not be removed. It will be appreciated by one skilled in the art that modifications can be made to the invention herein described without departing from the present inventive concept.

What is claimed is:

1. A method for decorating a substrate comprising applying a gold material to a substrate, said material comprising gold nanoparticles stabilised by thiol groups described by the general formula shown below, and further exhibiting a plasmon frequency of between 480 and 600 nm:

$$HSR$$

where:
R=is a $C_3$–$C_{60}$ alkyl group, aryl, benzyl, alicyclic, or heterocyclic group which may be substituted or unsubstituted, branched or unbranched.

2. The method according to claim 1 wherein R is a $C_3$–$C_{30}$ alkyl group, aryl, benzyl, alicyclic, or neterocyclic groups which may be branched or unbranched, substituted or unsubstituted.

3. The method according to claim 1 wherein R is substituted and wherein the substitution group is selected from the group consisting of carboxylate groups, esters, thioethers, ethers, amines, hydroxy amines, and amides.

4. The method according to claim 1 wherein R is an alkyl group, which may be branched or unbranched, substituted or unsubstituted.

5. The method according to claim 4 wherein R is substituted and the substituted groups are any one or more of the following:
—C(O)—OR" where R" is $C_1$–$C_{15}$ alkyl which may be branched or unbranched,
—C—O—R" or C—S—R" where R"=H or is $C_1$–$C_{15}$ alkyl which may be branched or unbranched,
—C—NR'R" where R' and/or R"=H or is $C_1$–$C_{15}$ alkyl which may be branched or unbranched
—C(O)—N—R'R" where R' and/or R"=H or is $C_1$–$C_{15}$ alkyl which may be branched or unbranched,
—aryl group
—SH group.

6. The method according to claim 1 wherein R is aryl.

7. The method according to claim 6 wherein the aryl group is benzene.

8. The method according to claim 7 wherein the benzene group is substituted in any one or more positions around the ring structure.

9. The method according to claim 8 wherein the substituents of the benzene group are $C_1$–$C_{15}$ alkyl groups which possess any one or more of the following features:
—C(O)—OR" where R" is $C_1$–$C_{15}$ alkyl which may be branched or unbranched,
—C—O—R" or C—S—R" where R"=H or is $C_1$–$C_{15}$ alkyl which may be branched or unbranched,
—C—NR'R" where R' and/or R"=H or is $C_1$–$C_{15}$ alkyl which may be branched or unbranched
—C(O)—N—R'R" where R' and/or R"=H or is $C_1$–$C_{15}$ alkyl which may be branched or unbranched,
—aryl group
—SH group.

10. The method according to claim 1 wherein R is benzyl which may be substituted in any one or more positions around the aromatic moiety and/or on the benzylic carbon, or may be substituted.

11. The method according to claim 1 wherein R is a nitrogen, phosphorus, sulphur or oxygen containing heterocycle group in which the thiol group is attached to a carbon group within said heterocycle ring structure.

12. The method according to claim 1 wherein R is $C_6H_4$-p-$CMe_3$, wherein H is hydrogen, S is sulphur, C is carbon, and Me is methyl.

13. A method for decorating a substrate surface comprising the steps of applying a gold material to a substrate surface, wherein said material comprises gold nanoparticles stabilised by thiol groups described by the general formula shown below, and further exhibiting a plasmon frequency of between 480 and 600 nm:

HSR wherein:
R=is a $C_1$–$C_{15}$ alkyl group, aryl, benzyl, alicyclic, or heterocyclic group which may be substituted or unsubstituted, branched or unbranched; and treating said substrate to adhere said gold material to the substrate surface to produce a decorative effect.

14. A method as claimed in claim 13 wherein the step of treating the substrate to adhere the gold material to the substrate does not involve firing.

15. A method as claimed in claim 13 wherein the substrate surface is selected from the group consisting of glass, earthenware, bone china, porcelain, silicate materials, metals, quartz, carbon, mica, plastics, laminates, wood, paper, textiles and leather.

16. A method as claimed in claim 13 wherein the step of applying the gold composition on the substrate surface is selected from the group of brush coating, ink-jet printing, stencilling, spraying, stippling, screen printing, spin coating, curtain coating, dip coating, pad printing, thermoplastic printing, wheel banding, decalcomania and electrostatic printing.

* * * * *